United States Patent

Samarasekera et al.

[11] Patent Number: 5,862,198
[45] Date of Patent: Jan. 19, 1999

[54] PRE-CALCULATED HITLIST FOR REDUCING RUN-TIME PROCESSING OF AN EXACT CONE BEAM RECONSTRUCTION ALGORITHM

[75] Inventors: Supun Samarasekera; Frank Sauer, both of Princeton; Kwok Tam, Edison, all of N.J.

[73] Assignee: Siemens Corporate Research, Inc., Princeton, N.J.

[21] Appl. No.: 940,924

[22] Filed: Sep. 30, 1997

[51] Int. Cl.[6] .................................................. A61B 6/03
[52] U.S. Cl. ................................................ 378/4; 378/901
[58] Field of Search ......................... 378/4, 901; 382/131; 600/425

[56] References Cited

U.S. PATENT DOCUMENTS

| | | | |
|---|---|---|---|
| 5,257,183 | 10/1993 | Tam | 378/4 |
| 5,333,164 | 7/1994 | Tam | 378/8 |
| 5,383,119 | 1/1995 | Tam | 378/8 |
| 5,390,112 | 2/1995 | Tam | 378/17 |
| 5,446,776 | 8/1995 | Tam | 378/4 |
| 5,461,650 | 10/1995 | Tam | 378/4 |
| 5,463,666 | 10/1995 | Eberhard et al. | 378/4 |
| 5,805,659 | 9/1998 | Tam | 378/15 |

Primary Examiner—David P. Porta
Assistant Examiner—David Vernon Bruce
Attorney, Agent, or Firm—Lawrence C. Edelman

[57] ABSTRACT

A method and apparatus for reconstructing an image of an object using a three dimensional (3D) computerized tomographic (CT) imager having a cone beam radiation source and detector arrangement for acquiring measurement data. Before the acquisition of measurement data during an imaging operation of the apparatus, image reconstruction processing information dependant on the geometric parameters of the imager and required for processing of the acquired measurement data for developing contributions to the final reconstruction of the image, is pre-calculated and stored. During an imaging operation of the apparatus, the acquired measurement data is processed using the pre-calculated image reconstruction processing information for reconstructing the image.

25 Claims, 3 Drawing Sheets

PRE-CALCULATED HITLIST FOR REDUCING RUN-TIME PROCESSING OF AN EXACT CONE BEAM RECONSTRUCTION ALGORITHM

BACKGROUND OF THE INVENTION

1. Field of the Invention

The present invention relates generally to computed tomographic (CT) imaging apparatus that performs three-dimensional (3D) image reconstruction by processing cone beam measurement data representative of an object, and more specifically, to calculating and storing before imaging operation of the apparatus, image reconstruction information dependant on geometric parameters of the imaging apparatus and required for processing of the acquired measurement data in accordance with a cone beam image reconstruction algorithm. During imaging operation of the apparatus, use of the pre-calculated information greatly speeds up the run-time processing of the image reconstruction algorithm.

2. Description of the Background Art

Recently a system employing cone beam geometry has been developed for three-dimensional (3D) computed tomographic (CT) imaging that includes a cone beam x-ray source and a 2D area detector. An object to be imaged is be scanned, preferably over a 360° angular range and along its length, by any one of various methods: i.e., by rotating the x-ray source in a scan path about the object while the object is being translated, by rotating and translating the source while the object remains stationary, or by rotating the object while one of the source or object is translated. These scanning techniques are all equivalent in that the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After acquisition, the measurement data is processed for reconstructing a 3D image of the object.

As compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source. Processing of the measurement data acquired using a cone beam source comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

As generally described in the forenoted U.S. Pat. No. 5,257,183, in order to provide a complete set of measurement data for accurate 3D (and even 2D) imaging of an object (or a region of interest in an object), it is necessary to satisfy completeness criteria. These criteria are well known, and are described in detail, for example, by Smith, B. D., in the publication "Image Reconstruction From Cone-Beam Projections, Necessary and Sufficient Conditions and Reconstruction Methods", IEEE Transactions Medical Imaging, MI-4 (1985), pp. 14–25. Basically, what is required is that any plane passing through the object or region of interest must intersect the scan path at one or more locations. The completeness criteria are also discussed in U.S. Pat. No. 5,383,119 entitled METHOD AND APPARATUS FOR ACQUIRING COMPLETE RADON DATA FOR EXACTLY RECONSTRUCTING A THREE-DIMENSIONAL COMPUTERIZED TOMOGRAPHY IMAGE OF A PORTION OF AN OBJECT RADIATED BY A CONE BEAM SOURCE issued on Jan. 17, 1995, hereby incorporated by reference. Additionally, this patent notes that the acquired data set is complete only if it can be processed so as to provide data at every point in the Radon space of a so-called "region of support". The "region of support" topologically corresponds to the field of view occupied by the region of interest of the object in real space. The Radon data is typically acquired by exposing the entire object within the field of view to an irradiating source.

As described in the forenoted U.S. Pat. No. 5,383,119, 3D image reconstruction techniques have difficulties imaging objects and regions which have a rather long or tall dimension. Generally, the detector must have a height and width large enough to cover the height and width of a projection of the object or region of interest on the detector, otherwise, some x-ray data would be missing. If the height or length of an object or region of interest is great, it is often impractical or difficult to obtain a detector array with sufficient height to obtain complete measurement data from the object or region of interest.

Sufficient filling of the Radon space by apparatus having various scanning trajectories (paths) and using an area detector which has a height that is less than the height of the region of interest being imaged are known for performing an exact image reconstruction. For example, in the above-noted U.S. Pat. No. 5,383,119, a rather complex technique is described for manipulating the acquired cone beam data so as to discard and recover data, as appropriate, so that only measurement data directly attributable to the region of interest is used for image reconstruction. In U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, a cone beam CT imaging system is disclosed in which a region of interest portion of an object can be imaged without blurring or artifact introduction from imaging portions of the object not within the region of interest. A controllably movable source and relatively small area detector are controlled so as to define a scan path consisting of a central spiral portion having one circle portion at each end of the spiral portion which is level with upper and lower boundaries, respectively, of the region of interest. The switch from a spiral path to a circular path is necessary in order to obtain complete cone beam data at the upper and lower boundaries of the region of interest without blurring caused by imaging portions of the object that are outside the region of interest, as described in greater detail in the forenoted U.S. Pat. No. 5,463,666.

U.S. Pat. No. 5,463,666 also describes a data combination processing technique useful in a 3D CT imaging system having a relatively small area detector. Briefly, to determine the value of each point in Radon space, measurement data acquired from each of several different source positions must be individually processed, each individual processing contributing a fractional amount to the final determination of the value.

Although the techniques noted above describe the theory for exactly reconstructing an image using cone beam measurement data, a practical implementation of the processing turns out to be quite problematic. Not only is the amount of measurement data to be processed very large and rapidly acquired, but the calculations required on the acquired data are quite complex. For example, if one decides to reconstruct an object with $200 \times 200 \times 200 = 8 \cdot 10^6$ (voxel=volume element of the object), for good quality one needs to obtain the object's 3-D Radon transform with a multiple (e.g., 4) amount of Radon samples, i.e., $32 \cdot 10^6$ samples, and then perform the Radon inversion. The most computationally expensive part of the object reconstruction is the calculation of the Radon derivative date (step 1 noted above). As noted in detail in the forenoted U.S. Pat. No. 5,463,666, measurement data from several source positions typically contribute to each Radon sample by way of data combination, thus one needs to calculate about $100 \cdot 10^6$ line integral derivatives. Each line integral derivative requires the calculation of $200 \cdot 10^6$ single line integrals, since one uses the difference between two closely spaced line integrals to calculate a single line integral derivative. However, before one can perform these line integral derivative calculations, one has to compute for each Radon sample which source positions will provide the measurement data that must be processed, and determine the lines on the measurement data along which the integration must be performed. These latter determinations involve highly nonlinear calculations and are therefore computationally costly. In order to compute the contributing source positions, one has to intersect the source scanning path with the Radon integration plane as explained in the forenoted U.S. Pat. No. 5,463,666. When using a spiral scan path, this requires the solution of transcendental equations, which are computationally expensive. Furthermore, in addition to determining the lines on the measurement data along which the integration must be performed, one also has to calculate the appropriate end points of those lines for data combination purposes and region-of-interest masking. The complexity of these above-noted calculations leads to severe bottlenecks in processing of the measurement data, so as to prevent rapid and efficient image reconstruction.

Additionally, since image reconstruction requires processing of Radon space data, but the data being acquired during the imaging operation of the apparatus is cone beam projected measurement data, the run-time (imaging operation) processing of the measurement data results in fragmentary development of the Radon data, thereby adding further complexity to the already severe processing difficulties.

It would be desirable to provide a method and apparatus for processing of the cone beam measurement data in a manner that reduces the above described computational complexities and difficulties, thereby allowing a more efficient implementation of an exact cone beam reconstruction algorithm.

Although the above-noted problems are already known, so far experts have only devised techniques for reducing the amount of measurement data that is to be processed. For example, U.S. Pat. Nos. 5,461,650 and 5,333,164 by Kwok C. Tam are representative of some of these prior art techniques. U.S. Pat. No. 5,461,650 entitled METHOD AND SYSTEM FOR PRE-PROCESSING CONE BEAM DATA FOR RECONSTRUCTION FREE OF INTERPOLATION-INDUCED ARTIFACTS A THREE DIMENSIONAL COMPUTERIZED IMAGE, issued Oct. 24, 1995, is representative of "masking" techniques wherein the amount of measurement data that is required for image reconstruction processing is truncated by defining areas on the detector array from which measurement data is to be discarded. U.S. Pat. No. 5,333,164 by Mr Kwok Tam entitled METHOD AND APPARATUS FOR ACQUIRING AND PROCESSING ONLY A NECESSARY VOLUME OF RADON DATA CONSISTENT WITH THE OVERALL SHAPE OF THE OBJECT FOR EFFICIENT THREE DIMENSIONAL IMAGE RECONSTRUCTION, issued Jul. 26, 1994, is representative of techniques for truncating the image reconstruction processing by selectively retaining for further processing only those Radon data points that are in the objects' Radon region of support. Although such truncations of the measurement data or the Radon data points results in an overall improvement in the speed of reconstructing an image, they do so by discarding data so it is not processed, not by improvement in the speed or efficiency of the processing of the actual measurement data that develops contributions to the final reconstruction of the image.

It would be desirable to provide an improvement in the speed or efficiency of the actual processing of the measurement data that develops contributions to the final reconstruction of the image.

SUMMARY OF THE INVENTION

In accordance with the principles of the present invention, before operation of a cone beam imaging apparatus for acquiring and processing of measurement data to reconstruct an image of an object, information required for processing of the acquired measurement data for developing contributions to the final reconstruction of the image, is pre-calculated and stored. The pre-calculated information is then used during the imaging operation of the cone beam apparatus for processing of the acquired measurement data for developing said contributions and reconstructing an image of the object. The pre-calculated image reconstruction information is organized into what is referred to hereinafter as a "hitlist". In general, the hitlist contains image reconstruction processing information that is determined primarily by geometric parameters of the imaging apparatus that are fixed during its imaging operation, and are independent of the measurement data, such as the pitch and other parameters of the source/detector scan path, the object dimensions, the detector resolution, and a desired sampling of the scan path and the Radon space. In the preferred embodiment the hitlist is ordered or sorted so as to indicate the correspondence between points in Radon space and the source positions that acquire data that can be processed to develop contributions thereto, and includes processing information parameters that define the line integrals that need to be calculated in the measurement data acquired at each of the source positions, as well as other information useful for reconstruction processing.

Although calculation of the hitlist information is computationally expensive, since the information in the hitlist must be calculated anyway in order to process each set of the acquired measurement data, its pre-calculation provides a very significant speed-up of the run-time (image) processing of the measurement data and results in a greatly improved efficiency in the implementation of the image reconstruction algorithm.

DETAILED DESCRIPTION OF THE PREFERRED EMBODIMENTS

Figure 1:
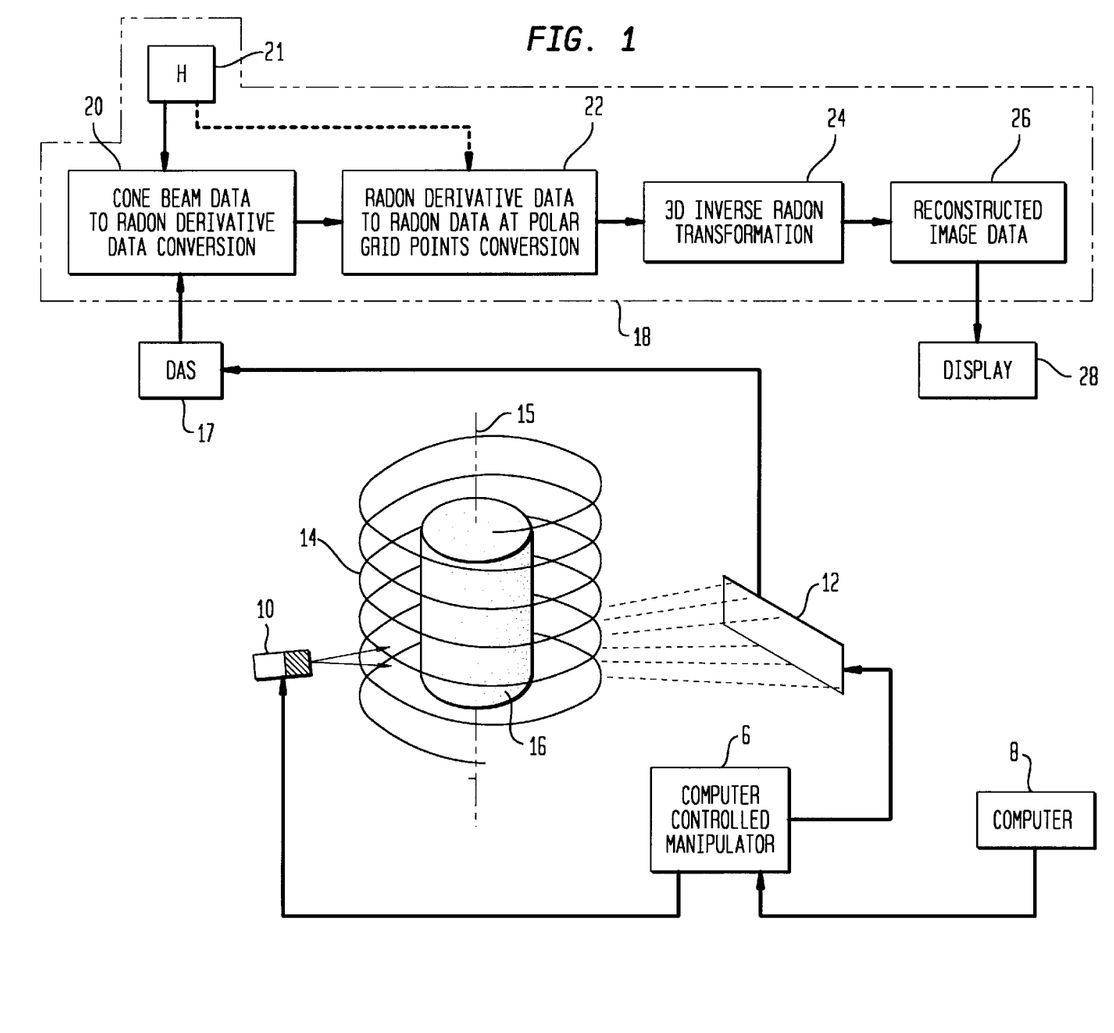
FIG. 1 is a block diagram and simplified perspective illustration of the imaging of an object using a cone beam imaging apparatus, wherein the apparatus uses a pre-calculated hitlist of reconstruction processing information for processing acquired measurement data in accordance with the principles of the present invention.

FIG. 1 illustrates a cone beam 3D CT imaging apparatus that operates in accordance with the principles of the present invention. Except as to be specifically described later with respect to implementation of image reconstruction processing in accordance with the present invention, the illustrated imaging apparatus is constructed and operates substantially the same as known in the forenoted U.S. Pat. No. 5,390,112. As generally illustrated in FIG. 1 herein, a computer controlled manipulator 6, in response to control signals from an appropriately programmed computer 8, causes a source 10 of cone beam energy (such as x-rays) and a two-dimensional array detector 12 to cooperate (scan) at a plurality of sequentially occurring source positions along a pre-defined source scanning path, illustrated as a spiral scan path 14 centered on a predetermined axis 15 of an object 16. As a result of the source/detector cooperation, detector 12 acquires complete cone beam measurement data which is then used for reconstructing an image of object 16. Alternatively, and equivalently, object 16 could be rotated and translated to cause scanning by a fixed position source and detector. Furthermore, the scanning can be accomplished in a continuous or stepwise manner, and the spiral path can have equally spaced turns (sometimes referred to as stages), or turns with decreasing pitch at the top and bottom edges of a region of interest of the object. Even furthermore, although source 10 is shown as an x-ray source, other types of imaging energy might be useful, such as neutrons, positrons, etc.

Computer 6, manipulator 8, source 10 and detector 12 cooperate to accomplish scanning of the object in a manner generally well understood by those skilled in this art, i.e., such as described in detail in the forenoted U.S. Pat. No. 5,390,112, and therefore discussion of further details of this portion of the operation of the cone beam imaging apparatus is deemed not necessary.

After the x-ray energy passes through the field of view of the imaging apparatus, measurement signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of measurement data corresponding to the acquired measurement signals.

The cone beam measurement data from the DAS 17 is supplied to a buffer memory and image reconstruction processor 18, which may be a computer programmed to perform various data conversions that process the measurement data so as to reconstruct an image, generally illustrated by the blocks within processor 18. More specifically, at block 20 the measurement data is processed so as to be converted to Radon derivative data at sample points in a Radon space partitioned by a plurality of vertically oriented $\psi$-planes. A spherical coordinate system is preferably used in this conversion to facilitate implementation of a Radon inversion procedure which follows. The conversion of block 20 may be accomplished, in general, using the techniques described in the forenoted U.S. Pat. No. 5,257,183. However, as will be described in greater detail later, in accordance with the principles of the present invention, the speed and efficiency of this portion of the image reconstruction processing is improved by use of a hitlist of pre-calculated image reconstruction processing information that is stored in a database 21, and used during run-time (imaging) operation of the apparatus for improving the speed and efficiency of this portion of the image reconstruction processing of the measurement data.

At block 22 the Radon derivative data is converted to Radon data at polar grid points on the $\psi$-planes using, for example, the technique described in detail in conjunction with FIG. 5 of the forenoted U.S. Pat. No. 5,446,776. Briefly, as described therein, the Radon derivative data is converted to Radon derivative data at equally spaced polar grid points using nearest neighbor or interpolation techniques, and then integrated to develop the Radon data at equally spaced polar grid points. The hitlist of reconstruction processing information stored in database 21 preferably also provides pre-calculated information during this portion of the reconstruction processing (as indicated by the dashed line from database 21 to block 22), such as weighting information used for interpolation processing, thereby also improving the speed and efficiency of this portion of the reconstruction processing.

At block 24 the Radon data is subjected to inverse 3D Radon transformation processing using well known techniques, such as those described in detail in the forenoted U.S. Pat. No. 5,257,183, thereby developing and storing at block 26 reconstructed image data. The reconstructed image data is then fed from reconstruction processor 18 to a display 28, which may operate in known fashion, to provide 3D CT imaging of object 16.

Except for the determination and use of the hitlist, a more detailed description of the blocks of FIG. 1 can be found in the forenoted patents incorporated by reference herein.

As previously noted, the exact cone beam reconstruction algorithm as described in U.S. Pat. No. 5,257,183 is based on the calculation of line integrals for determining Radon data of the x-rayed object.

Figure 2:
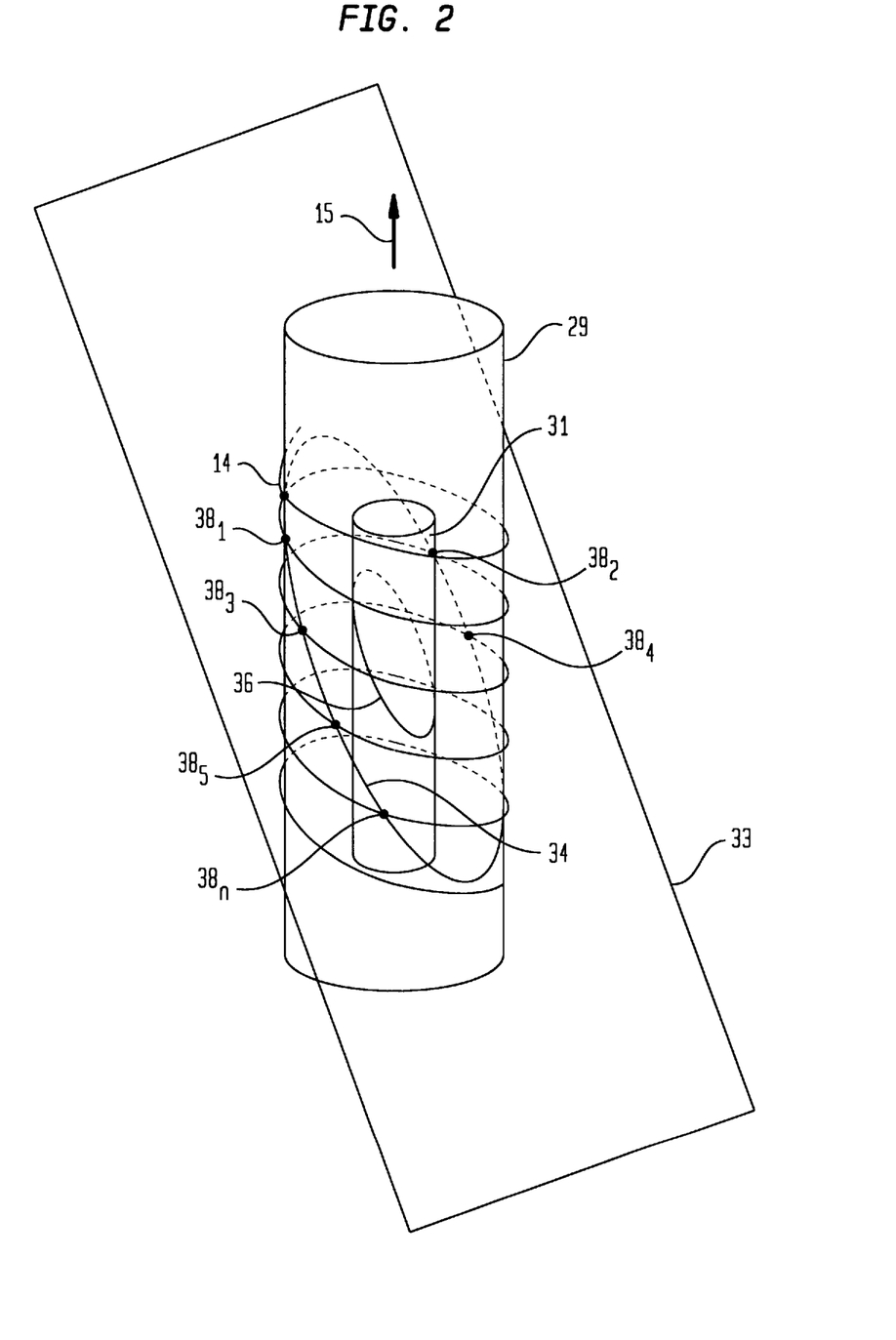
FIG. 2 illustrates an isometric view of an exemplary planar intersection of a field of view of the imaging apparatus of FIG. 1, useful for understanding the present invention.
Figure 3:
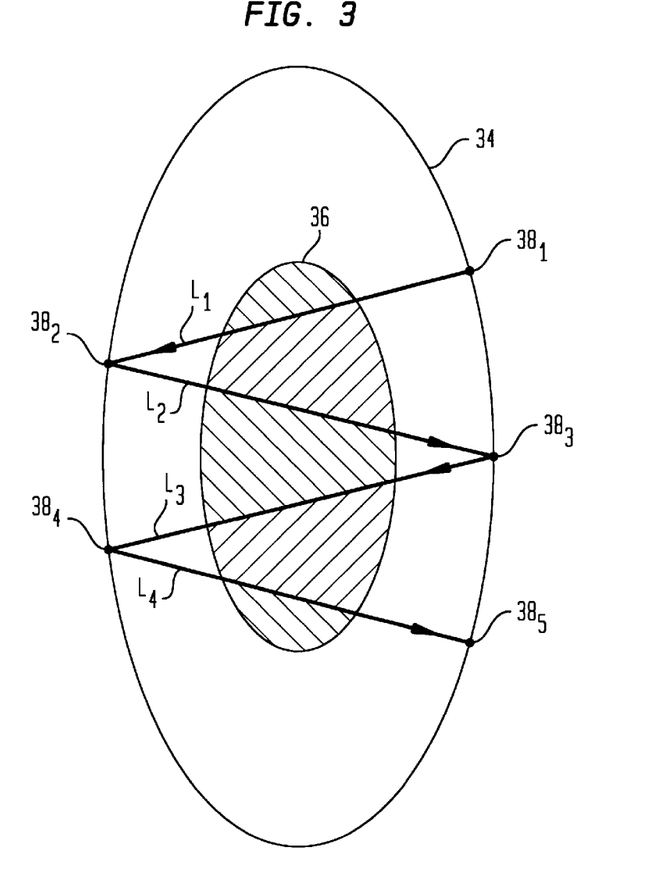
FIG. 3 illustrates a section view of the planar intersection shown in FIG. 2.

In order to determine which line integrals and line integral derivatives to calculate, from which portions of the acquired measurement data the calculations are to be made, and to which sample point in Radon space each of the calculated line integral derivatives contributes, reference is now made to FIGS. 2 and 3.

As shown in FIG. 2, the spiral scan path 14 is located on a geometric surface, such as a cylinder 29, radially centered on the longitudinal axis 15 of a maximal object volume 31 allowed by the field of view of the imaging system that includes object 16 (not shown). Such field of view is sometimes referred to as the "object's region of support". Any plane 33 intersecting the region of support 31 must also intersect the boundary of the geometric surface which surrounds the object, since scan path 14 is defined upon such geometric surface. In the illustrated embodiment, the geometric surface corresponds to the surface of cylinder 29. Thus, the curve of intersection between plane 33 and cylinder 29 is an ellipse, identified by numeral 34. FIG. 2 also shows that the curve of intersection between plane 33 and cylindrical field of view 31 is also an ellipse, identified by numeral 36, which is enclosed by scanning ellipse 34. Consequently, since scan path 14 lies on the surface of cylinder 29, scan path 14 intersects plane 33 at a plurality of points, identified as points $38_1 \ldots 38_n$ that collectively lie on the boundary of the geometric surface upon which the helical path is defined, that is, such points of intersection lie on scanning ellipse 34.

As described more fully in FIGS. 3–10 of the forenoted U.S. Pat. No. 5,257,183, 3D Radon transform datum at a given point in object 16 can be uniquely determined by the planar integral of the object's x-ray attenuation coefficient. The integration plane is that plane which passes through the given Radon point and is perpendicular to a line from the Radon origin to the Radon point. In order to reconstruct an image of an object within the region of support 31, Radon data for the portion of an integration plane 33 that lies within the region of support is used. However, because of the geometry of the cone beam projection, this portion of integration plane 33 does not correspond directly to the object's Radon transform, but instead the derivative of the line integrals on the measurement data corresponds to the radial derivative of the Radon transform. Consequently, before inverse Radon transformation can be accomplished, the data conversions provided by blocks 20 and 22 are required.

As conceptually illustrated in FIG. 3, the required Radon derivative data at the given point determined by block 20 of FIG. 2 can be obtained by appropriate processing of multiple sets of cone beam measurement data, each of the sets being acquired at a corresponding one of a plurality of source/detector positions along the scan path. Each position corresponds to a point of intersection of scan path 14 and plane 33, i.e, points $38_1$ to $38_n$ (illustrated in FIG. 2). In the exemplary illustration, the measurement data acquired at five different scan positions, corresponding to five points of intersection, are used to generate a complete data set which can be processed for determining one Radon data point, subsequent determination of many of such Radon points then being used for reconstructing a three-dimensional image of the object.

As shown therein, the region bounded within ellipse 36 corresponds to the portion of plane 33 which intersects region of support 31 enclosing the object being imaged. As illustrated by cross-hatching therein, region 36 can be considered to comprise five partial planes, each partial plane being bounded by a region of support of the scanning apparatus at a different point of intersection. For example, at a scan position corresponding to intersection point $38_1$, a set of cone beam measurement data is acquired that includes measurement data for the portion of plane 33 located above line $L_1$, i.e., that portion of the turn of scan path 14 that is bounded by points $38_1$ and $38_2$. At the scan position corresponding to point $38_2$, a set of cone beam measurement data is acquired that includes measurement data for the portion of plane 33 located between lines $L_1$ and $L_2$, i.e., the portion of scan path 14 that is bounded by points $38_1$ and $38_3$. At the scan position corresponding to point $38_3$, a set of cone beam measurement data is acquired that includes measurement data for the portion of plane 33 located between lines $L_2$ and $L_3$, i.e., the portion of scan path 14 that is bounded by points $38_2$ and $38_4$. At the scan position corresponding to point $38_4$, a set of cone beam measurement data is acquired that includes measurement data for the portion of plane 33 located between lines $L_3$ and $L_4$, i.e., the portion of scan path 14 that is bounded by points $38_3$ and $38_5$. Finally, at the scan position corresponding to point $38_5$, a set of cone beam measurement data is acquired that includes measurement data for the portion of plane 33 located below line $L_4$, i.e., that portion of scan path 14 that is bounded by points $38_4$ and $38_5$. Since the five partial planes in the foregoing five scan positions do not overlap (i.e., they do not form an overlying portion within the region of support 31) and collectively they completely cover the portion of plane 33 that intersects the region of support in which the object being imaged is situated, the combination of such partial integration planes of the acquired multiple sets of measurement data can be used to calculate the Radon datum in an exact way, making it possible to exactly reconstruct an image of the object without introducing data corruption.

However, as previously described, the calculations required for determining the Radon data are quite complex, and in view of the fact that processing of cone beam measurement data acquired at several source positions is required for determining the numerical value of the Radon data at a given Radon sample point, and the measurement data at those required source positions are not supplied adjacent one another in time, further processing complexities and inefficiencies are also introduced.

In analyzing this problem, the present inventors realized that calculation of the Radon derivative data from the cone beam measurement data can be functionally subdivided into two parts, as follows:

| | |
|---|---|
| Part 1 | determining for each desired Radon space sample point, which sets of the measurement data can be processed to determine a contribution to the Radon value at that point, determining which line integral derivatives on each of the determined data sets need to be calculated for contributing to the previously determined Radon points, and how each of the calculated line integral derivatives contribute thereto. |
| Part 2 | performing line integral derivative calculations, as indicated by the determinations noted above, on the cone beam measurement data, and storage of the results for each of the desired Radon points. |

Subdivided in this manner, the present inventors came upon the realization that although the Part 1 determinations are needed in order to process the measurement data, the required calculations are in fact independent of the acquired measurement data (i.e., the calculations do not require actual processing of the measurement data), such as those calculations that are determined solely by the geometry of the scanner apparatus, the desired sampling of the source path (i.e., number of source positions), and the desired sampling of the Radon space. On the other hand, the Part 2 calculations require processing of the acquired measurement data for developing contributions to the finally reconstructed image.

In accordance with the principles of the present invention, the information required for the Part 1 determinations are pre-calculated and stored in a database, referred to hereinafter as a hitlist 21 (FIG. 1). For each source position on scan path 14 (i.e. for each set of the measurement data), hitlist 21 may contain the following information: the Radon space sample points to which that particular data set contributes, and parameters that define the corresponding line integrals which have to be performed for contributing to those Radon space sample points.

Hitlist 21 can be implemented as a database, an in accordance with a further aspect of the present invention, have its information sorted according to the time sequential occurrence of the source scan positions. That is, for example, at a given source position, the hitlist information identifies all the Radon points that the measurement data acquired at that source position contributes, and information that would enable processing of that measurement data to determine a contributing amount of derivative Radon data (a numerical value) for each of those Radon points. For processing the measurement data, that information includes defining integration lines, as well as start and end points on those integration lines for providing masking information and defining which Radon points that data will contribute to.

In a preferred embodiment it is advantageous to order the hitlist information in database 21 in a source driven way (i.e. sorted source position by source position), since this is the way the measurement data becomes available for processing during image operation of the apparatus. Furthermore, database 21 can be organized so that the hitlist information for a given source position may be sorted even further, for example, by the Radon points therein. This further sorting would allow one to reconstruct an object at different resolutions, for example a lower resolution, if desired, by simply using the information from a subset of the database, and thereby substantially reducing the amount of calculations that need to be performed. This mode of operation of the invention allows one to initially operate the imaging apparatus in a lower resolution, but higher speed, mode. This mode of operation may be useful, for example, for locating or centering a desired region of interest of an object, and thereafter switching operation of the imaging apparatus to a higher resolution mode. Additionally, the Radon points in the database may be sorted radially, so as to allow database 21 to supply processor 18 only reconstruction information that is appropriate for the Radon region of support given the size of the object being imaged.

Furthermore, since the Radon space is sampled in a known manner, one need not store the actual coordinates of the Radon sample points, and instead one can store indices corresponding thereto, which reduces the storage space requirements of the hitlist.

Depending on the amount of storage space available, one can store more or less information (respectively more or less parameters), requiring more or less calculation at runtime.

Figure 4:
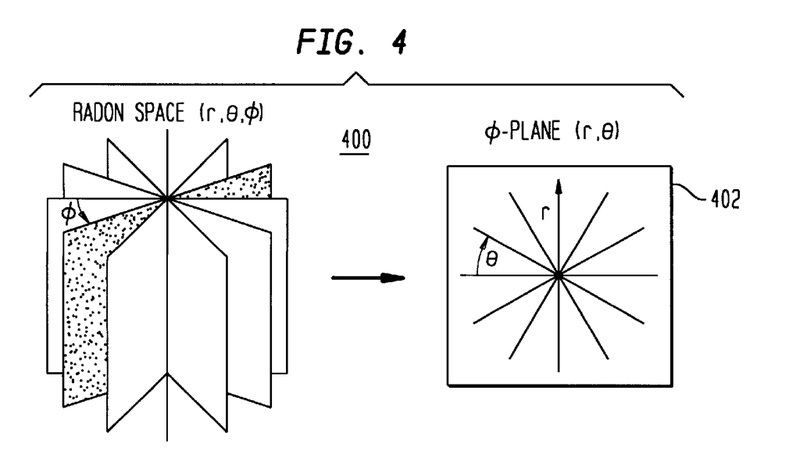
FIG. 4 illustrates sampling of the Radon space in a spherical coordinate system.

Reference is now made to FIG. 4 for description of the construction of the hitlist database 21. It is well known to those skilled in this technology, that inverse Radon transform processing of Radon data at polar grid points will provide the desired end result of reconstruction of an image of an object. To reconstruct an object with a given resolution in object space (x,y,z), a multiple sampling, such as 4, is required in Radon space (r,θ,ψ). Thus, the hitlist information is calculated in a Radon space driven arrangement. FIG. 4 illustrates how Radon space in spherical coordinates can be partitioned by a set of vertically oriented coaxial planes 402, each of ψ-planes 402 being sampled in polar coordinates, as shown. For ease of illustration only a few coaxial ψ-planes are shown, while in an example of a practical implementation, 360 such ψ-planes spaced at ½ degree intervals could be utilized. As explained in greater detail in the forenoted US patents, the Radon data should be determined on the polar grid points of a polar grid in order to perform the required inverse Radon transformation processing. The maximum size of the object determines the maximum size of the object's support in Radon space which has to be taken into consideration. Sampling of this Radon space leads to a predetermined finite number of Radon points. Then, for each of these Radon points, the next step is to calculate which source positions will acquire measurement data that can be processed to develop a portion of the Radon data that will contribute to the given Radon point, and exactly which processing is required, for example, which specific line integral derivatives need to be calculated.

The source positions which contribute to a given Radon point are calculated by calculating the intersections between the integration plane which corresponds to the given Radon point, with the source scan path, such as previously described in conjunction with FIGS. 2 and 3. Ideally, one would like to have measurement data taken with the source being at these exact intersections. However, in practice the actual scan path sampling does not exactly corresponded to these calculated ideal intersections. Thus, one may choose the actual source position which come closest to each of the ideal positions, called a nearest neighbor approach, or an interpolation approach where measurement data at the two actual source positions which are closest to each ideal position are combined in a weighted manner to develop the measurement data at the ideal position. Use of both these techniques is described in greater detail in conjunction with FIG. 5 of the forenoted U.S. Pat. No. 5,446,776. Consequently, the hitlist information for each Radon point may also include parameters defining lines on the detector along which line integral derivative calculations are to be made, parameters defining the start and end points of these lines (including masking information), and parameters defining how the line integral derivative calculations are to be made (i.e., use of parallel or angled lines, the line segments and number of line integral derivatives to be used for determining each derivative value, and interpolation and weight information).

This Radon space driven hitlist is then re-sorted, in accordance with an aspect of the present invention, into a source space driven version, where the reconstruction processing information is ordered source position by source position, i.e., the order by which the measurement data is acquired during the imaging operation of the apparatus.

The source position driven version of the hitlist is stored as a database 21, as previously shown and described in conjunction with FIG. 1, for use during imaging operation of the apparatus for processing of the acquired measurement data to develop contributions for image reconstruction. The availability of the hitlist information organized as described, speeds-up the reconstruction time in a very significant way.

Thus, there has been shown and described a novel method and apparatus for greatly speeding-up and improving the efficiency of the image reconstruction processing in a cone beam 3D CT imaging apparatus. Many changes, modifications, variations and other uses and applications of the subject invention will, however, become apparent to those skilled in the art after considering this specification and its accompanying drawings, which disclose preferred embodiments thereof. For example, although in practice a spiral scan path (as shown) may be the most practical, any pre-determined scan path or geometric configuration of the scanning apparatus can be used in conjunction with the invention.

Furthermore, information in addition to that already described could be stored in the hitlist for later use, and the stored information could be further sorted in ways different From that already described, for further facilitating the image reconstruction processing. Additionally, although a database 21 is described for storing the hitlist information, other types or arrangements of data storage could be used.

All such changes, modifications, variations and other uses and applications which do not depart from the general teaching of the invention herein, are deemed to be covered by this patent, which is limited only by the claims which follow as interpreted in light of the foregoing description.

What is claimed is:

1. A method of operating a 3D CT imaging apparatus having a cone beam radiation source and detector arrangement, for reconstructing an image of an object that is scanned by said source and detector arrangement, comprising the following steps:
    before the acquisition of measurement data during an imaging operation of the apparatus,
    pre-calculating and storing image reconstruction processing information required for processing of the acquired measurement data to develop contributions to the final reconstruction of the image, which information is dependant on the geometric parameters of the imager and independent of the measurement data; and
    during the imaging operation of the apparatus,
    operating said source and detector arrangement at a plurality of source positions along a scan path so as to acquire a corresponding plurality of sets of said measurement data, and
    processing the acquired measurement data using said pre-calculated image reconstruction processing information for developing said contributions and reconstructing the image.

2. The method of claim 1, wherein said pre-calculating and storing step comprises,
    calculating as said image reconstruction processing information that information which is determined by pre-determined geometric parameters of the scan path and the detector, and a desired sampling of the scan path and Radon space.

3. The method of claim 1, wherein said processing step develops numerical values for a plurality of sample points in Radon space in response to reconstruction information supplied thereto from said database for developing contributions to said image reconstruction, said database information being further sorted so as to supply to said processing step a subset of its information for causing said processing step to develop a subset of said sample points.

4. The method of claim 1, wherein said pre-calculating and storing step comprises,
    organizing the pre-calculated image reconstruction processing information into a database.

5. The method of claim 4, wherein:
    said operating step operates the source and detector arrangement at a plurality of spatially adjacent source positions along the scan path so as to cause acquisition of said corresponding plurality of sets of measurement data in a time sequential order, and
    said processing step processes the acquired measurement data in the time sequential order that they are acquired, in conjunction with said database having said image reconstruction processing information sorted therein by the time sequential order of the acquisition of said sets of measurement data.

6. The method of claim 5, wherein said processing step develops numerical values for a plurality of sample points in Radon space in response to reconstruction information supplied thereto from said database for developing contributions to said image reconstruction, said database information being further sorted so as to supply to said processing step a subset of its information for causing said processing step to develop a subset of said sample points.

7. The method of claim 6, comprising the further step of:
    controllably sorting said database by said sample points so as to only supply to said processing step reconstruction information which will reconstruct the image in a desired resolution.

8. The method of claim 6, comprising the further step of:
    controllably sorting said database by said sample points so as to only supply to said processing step reconstruction information for a region of support in Radon space which is appropriate for the size of the object being imaged.

9. The method of claim 1, wherein said pre-calculating and storing step comprises,
    calculating as said image reconstruction processing information that information which indicates the correspondence between sample points in Radon space and the source positions that develop measurement data that can be processed to contribute numerical values thereto.

10. The method of claim 9, wherein said pre-calculating and storing step includes,
    defining a plurality of planes, each one of which will pass through a field of view of the imaging apparatus and intersect the scan path in at least one point as well as the detector, for determining the correspondence between sample points and the source positions from which the contributions thereto can be developed.

11. The method of claim 10, wherein said pre-calculating and storing step includes,
    calculating as said image reconstruction processing information parameters that define line integral derivatives that need to be calculated in the acquired measurement data for contributing to the numerical value of said sample points.

12. The method of claim 10 wherein said image reconstruction processing information includes masking and line parameters.

13. A method of operating a 3D CT imaging apparatus having a cone beam radiation source and detector arrangement, for reconstructing an image of an object that is scanned by said source and detector arrangement, comprising the following steps:
    before the acquisition of measurement data during an imaging operation of the apparatus,
    pre-calculating and storing image reconstruction processing information required for processing of the acquired measurement data to develop contributions to the final reconstruction of the image, which information is stored in an organized format that indicates the correspondence between sample points in Radon space and the source positions that develop measurement data that can be processed to contribute numerical values thereto; and during the imaging operation of the apparatus, operating said source and detector arrangement at a plurality of source positions along a scan path so as to acquire a corresponding plurality of sets of said measurement data, and processing the acquired measurement data using said pre-calculated image reconstruction processing information for developing said contributions and reconstructing the image.

14. The method of claim 13, wherein said pre-calculating and storing step comprises, organizing the pre-calculated image reconstruction processing information into a database.

15. The method of claim 14, wherein:

said operating step operates the source and detector arrangement at a plurality of spatially adjacent source positions along the scan path so as to cause acquisition of said corresponding plurality of sets of measurement data in a time sequential order, and said processing step processes the acquired measurement data in the time sequential order that they are acquired, in conjunction with the organized format of said database information being sorted by the time sequential order of the acquisition of said sets of measurement data.

16. The method of claim 15, wherein said processing step develops numerical value contributions for a plurality of sample points in Radon space in response to reconstruction information supplied thereto, the organized format of said database information being further sorted so as to supply to said processing step a subset of its information for causing said processing step to develop a subset of said sample points.

17. The method of claim 16, comprising the further step of:

controllably sorting said database by said sample points so as to only supply to said processing step reconstruction information which will reconstruct the image in a desired resolution.

18. The method of claim 16, comprising the further step of:

controllably sorting said database by said sample points so as to only supply to said processing step reconstruction information for a region of support in Radon space which is appropriate for the size of the object being imaged.

19. A scanning and data acquisition apparatus for three dimensional (3D) computerized tomography (CT) imaging of an object in a field of view radially centered on a predetermined axis, comprising:

an energy source (10) for emitting energy in the form of a cone beam;

an area detector (12) for detecting as measurement data cone beam energy after attenuation by passage through an object to be imaged;

a manipulator (6) for movably positioning said source and detector along a scan path relative to the object, to cause irradiation of said object by said source at multiple source positions along said scan path about said object, said detector acquiring a corresponding set of measurement data at each said source position;

control means (8) for defining the scan path as a plurality of spaced stages on a predetermined geometric surface surrounding the field of view, with each of a plurality of planes that pass through the field of view and intersect the scan path in at least one point as well as the area detector, being useful for calculating Radon data at a given one of a plurality of Radon sample points;

image reconstruction processing means (18) including means for calculating Radon data for each of said Radon sample points by processing multiple ones of the sets of measurement data, for developing image data; and display means (28) responsive to said image data for displaying a reconstructed image of the object;

wherein said image reconstruction processing means (18) includes a database (21) of reconstruction processing information that is dependant on the geometric parameters of the imager, which information is precalculated and stored before acquisition of the measurement data, and then used by said image reconstruction processing means (18) during imaging operation of said apparatus for facilitating processing of the measurement data to calculate the Radon data.

20. Apparatus in accordance with claim 19, wherein said image reconstruction processing means (18) includes Radon derivative calculating means (20) responsive to the image reconstruction processing information stored in said database (21) for calculating Radon derivative data for each of said Radon sample points by processing line integral values from multiple ones of the sets of measurement data.

21. Apparatus in accordance with claim 19, wherein said image reconstruction processing means (18) includes Radon derivative data converting means (22) responsive to the image reconstruction processing information stored in said (database 21) and said Radon derivative data for calculating Radon data at equally spaced polar grid points.

22. Apparatus in accordance with claim 19, wherein said image reconstruction processing means (18) includes inverse transformation processing means (24) responsive to said Radon data at equally spaced polar grid points for performing a 3D inverse Radon transformation of said Radon data to and develop said image data.

23. Apparatus in accordance with claim 19, wherein said image reconstruction processing means (18) is response to said database (21) so as to develop numerical values for a plurality of sample points in Radon space in response to reconstruction information supplied thereto from said database.

24. Apparatus in accordance with claim 23, wherein said image reconstruction processing means (18) includes means for causing said database (21) to supply to said processing means (18) a subset of its information, thereby causing said processing means (18) to develop a subset of said sample points.

25. Apparatus in accordance with claim 23, wherein said manipulator positions the energy source (10) at a plurality of spatially adjacent source positions along the scan path so as to cause acquisition of said corresponding sets of measurement data in a time sequential order, and said database (21) provides said image reconstruction processing information to said processing means in said time sequential order, thereby enabling said processing means to process the acquired measurement data in the time sequential order that they are acquired.

* * * * *